(12) United States Patent
Hu et al.

(10) Patent No.: US 10,611,888 B2
(45) Date of Patent: Apr. 7, 2020

(54) PROCESSES OF INCREASING CRYSTALLINITY ALIGNMENT OF PROTEIN FILMS AND PRODUCTS THEREOF

(71) Applicant: Rowan University, Glassboro, NJ (US)

(72) Inventors: Xiao Hu, Glassboro, NJ (US); Sam Lofland, Glassboro, NJ (US)

(73) Assignee: Rowan University, Glassboro, NJ (US)

( * ) Notice: Subject to any disclaimer, the term of this patent is extended or adjusted under 35 U.S.C. 154(b) by 102 days.

(21) Appl. No.: 15/567,891

(22) PCT Filed: Apr. 25, 2016

(86) PCT No.: PCT/US2016/029175
§ 371 (c)(1),
(2) Date: Oct. 19, 2017

(87) PCT Pub. No.: WO2016/172689
PCT Pub. Date: Oct. 27, 2016

(65) Prior Publication Data
US 2018/0105659 A1    Apr. 19, 2018

Related U.S. Application Data

(60) Provisional application No. 62/151,560, filed on Apr. 23, 2015.

(51) Int. Cl.
*C08J 5/18*        (2006.01)
*C07K 1/36*       (2006.01)

(52) U.S. Cl.
CPC ........ *C08J 5/18* (2013.01); *C07K 1/36* (2013.01); *C08J 2389/00* (2013.01)

(58) Field of Classification Search
None
See application file for complete search history.

(56) References Cited

U.S. PATENT DOCUMENTS

| | | |
|---|---|---|
| 4,264,493 A | 4/1981 | Battista |
| 6,395,198 B1 | 5/2002 | McArdle |
| 7,285,637 B2 | 10/2007 | Armato et al. |
| 2014/0094410 A1 | 4/2014 | Kaplan et al. |

OTHER PUBLICATIONS

Zhang et al., "Preparation and characterization of silk fibroin as a biomaterial with potential for drug delivery", Journal of Translational Medicine 10: 117 (2012) (Year: 2012).*
Sasithorn et al., "Effect of Calcium Chloride on Electrospinning of Silk Fibroin Nanofibers," RMUTP International Conference: Textiles & Fashion (Jul. 2012); pp. 1-8.
Hu et al., "Charge-lunable silk-tropoelastin protein alloys that control neuron cell responses," Adv. Funt. Mater (Aug. 19, 2013); 23(31):3875-3884.

* cited by examiner

*Primary Examiner* — Anand U Desai
(74) *Attorney, Agent, or Firm* — Saul Ewing Arnstein & Lehr LLP; Domingos J. Silva; Justin W. Crotty

(57) ABSTRACT

A method of processing a protein in an acid solution is disclosed. The processed protein exhibits various optimized properties including crystallinity, thermal stability, bio-stability, and elastic modulus.

40 Claims, 9 Drawing Sheets

PROCESSES OF INCREASING CRYSTALLINITY ALIGNMENT OF PROTEIN FILMS AND PRODUCTS THEREOF

CROSS-REFERENCE TO RELATED APPLICATIONS

This application claims priority under 35 U.S.C. § 119 to U.S. Provisional Patent Application Ser. No. 62/151,560, filed on Apr. 23, 2015, which is hereby incorporated by reference in its entirety.

FIELD OF THE INVENTION

The present invention is directed to methods of processing protein-based polymer materials. The processed proteins demonstrate tunable properties and find applications in various fields.

BACKGROUND

Polymer materials with good physical properties have an enormous market and find applications in various fields. However, most of the existing materials have one or more defects. Many of the polymer products in the market today are very hard or brittle and cannot be manipulated easily with tunable physical properties. In addition, some of them are not environment-friendly. For example, many synthetic polymer materials are flammable or have a tendency to produce toxic residues. While some of the recently reported processes sought to minimize these drawbacks (see for example Zhang, et al., ACS Appl Mater Interfaces 2015; 7(5):3352-61), there still exist issues in product quality and cost efficiency.

It is thus desirable to develop an environmentally friendly process for the production of bio-materials with low cost and high mechanical flexibility.

SUMMARY

The present invention meets such need. One aspect of the invention provides a method of processing a protein comprising the steps of: dissolving a protein in a solution; optionally allowing the solution to sit for a desirable period of time; removing insoluble materials or impurities from the solution; casting the solution in a container; and removing the solvent to obtain a processed protein. In some embodiments, the protein is pre-treated by degumming to remove undesirable components.

In some embodiments, the method further includes applying pressure to the above processed protein.

In some embodiments, the protein is derived from a source including Indian *Antheraea mylitta* silk (Tussah), *Philosamia ricini* silk (Eri), *Antheraea assamensis* silk (Muga), Thailand silk (Thai), Chinese *Bombyx mori* mulberry silk (Mori), corn zein protein (zein), or combination thereof. In some embodiments, the protein is selected from collagen, elastin, keratin, and silk.

In some embodiments, the content of the protein in the solution is in the range of about 0.1%-40% w/v. In some embodiments, the protein solution contains about 0.001 g/ml-0.5 g/ml of protein.

In some embodiments, the protein solution further includes another material such as metals, chemicals and/or pharmaceutical agents.

Another aspect provides a protein obtained from the methods of the present invention.

DETAILED DESCRIPTION

Figure 1:
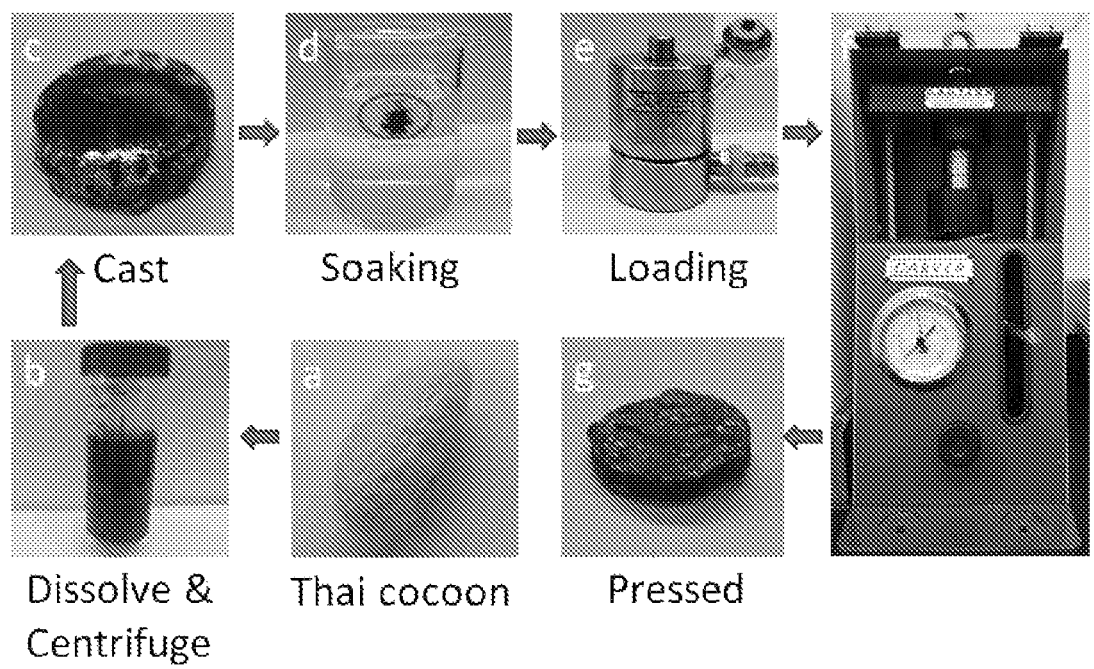
FIG. 1 depicts a schematic diagram for the fabrication of a raw protein material (a) into a thin film (f) (Thai silk as an example).
Figure 2:
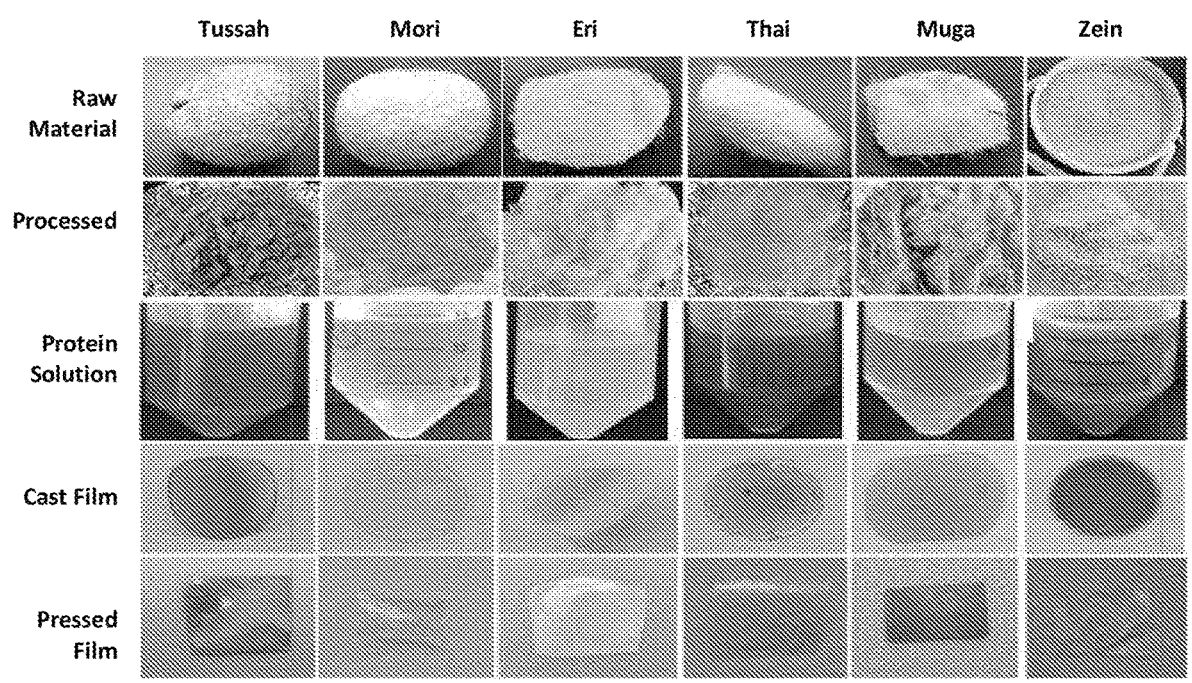
FIG. 2 depicts the appearance and shape of proteins at different stages: raw silks (Tussah, Mori, Eri, Thai, Muga), prepared silk (silk fibroin fibers after removal of the glue-like sericin proteins), silk solution, and cast films (top to bottom).
Figure 3:
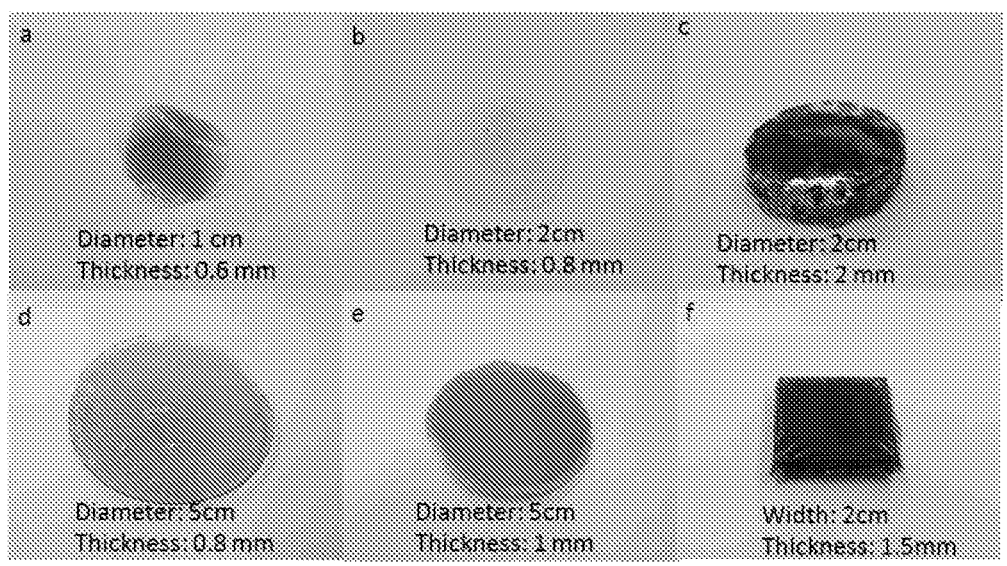
FIG. 3 depicts protein samples with different thickness and diameter (width).

Various embodiments of the present invention provide methods of processing a protein. Conventional means of protein processing is often time-consuming but the effect on the end product is limited. By contrast, the present invention employs a cost-effective process and allows for manipulation of properties such as crystallinity structure, thermal degradation temperature, bio-stability, and mechanical strength.

One aspect of the invention provides a method of processing protein. The method includes the steps of: dissolving a protein in a solution; optionally allowing the solution to sit for a desirable period of time; removing or insoluble materials or impurities from the solution; casting the solution in a container; and removing the solvent to obtain a processed protein. In some embodiments, the method further includes applying pressure to the above processed protein. Compressing the protein leads to higher crystallinity/structures and crystal alignments due to molecular re-alignment under pressure.

Proteins processed with the present invention can be derived from various sources. Examples include silks from worm species, keratins from hairs and wools, tissue elastins, collagens, resilins, reflectins, and plant proteins. Other non-limiting examples of the protein source include Indian *Antheraea mylitta* silk (Tussah), *Philosamia ricini* silk (Eri), *Antheraea assamensis* silk (Muga), Thailand silk (Thai) and Chinese *Bombyx mori* mulberry silk (Mori), corn zein protein (zein), and derivatives or analogs thereof.

The protein may be natural, synthetic or recombinant. For example, the protein may be a natural or recombinant silk protein from different silkworm species. Further, the protein can be modified by methods known in organic chemistry to incorporate or remove certain groups. In some embodiments, the protein is modified by methods known in organic chemistry to incorporate or remove certain groups. Thus, materials that can be processed with the present method also include peptides linked to other chemical structures such as a PEG, a linker, and a functional group. Preferably before being dissolved in a solution, the protein is degummed to remove undesirable components (e.g. soluble silk sericin proteins coated on most silk fibroin fibers) using procedures known in the art to remove undesirable components (e.g. soluble silk sericin proteins coated on most silk fibroin fibers). Other purification or washing step can also be performed to remove the impurities.

In some embodiments, two or more proteins are dissolved in a solution to prepare a protein alloy biomaterial. For example, a protein from wild tussah silk and a protein from domesticated mulberry silk can be dissolved in the same solution and processed according to methods of the present invention to obtain a biomaterial of unique mechanical properties.

The method may also include a step of adding materials/agents to modify the structure of the protein or provide additional function. Examples of the materials/agents include graphene, nanotubes, nanofibers, nanoparticles, salts, metal particles, chemicals and/or pharmaceutical agents.

The amount of a protein in the solution may vary. Exemplary ranges include about 0.1%-about 60% w/v, about 1%-about 40% w/v, about 1%-about 30% w/v, about 1%-about 20% w/v, about 1%-about 10% w/v, about 2%-about 40% w/v, about 2%-about 30% w/v, about 2%-about 20% w/v, about 2%-about 10% w/v, about 5%-about 40% w/v, about 5%-about 30% w/v, about 5%-about 20% w/v, and about 5%-about 10% w/v, all subunits and sub-ranges included. Non-limiting examples of the protein content include about 0.1%, 0.5%, 1%, 2%, 3%, 4%, 5%, 6%, 7%, 8%, 9%, 10%, 12%, 14%, 16%, 18%, 20%, 25%, 30%, 35% 40%, 45%, 50%, 55%, and 60% w/v. Other example ranges of protein include about 0.001 g/ml-0.5 g/ml, all subunits and sub-ranges included. Non-limiting examples of the protein content include about 0.001, 0.005, 0.01, 0.02, 0.03, 0.04, 0.05, 0.06, 0.07, 0.08, 0.09, 0.1, 0.2, 0.3, 0.4, 0.5, and 0.6 g/ml.

The solutions for dissolving the protein generally contain a solute of a salt of an alkali metal (e.g. Li, Na, K) or alkaline earth metal (Ca, Mg) and an acid as the solvent. The anions of the salt can be any of the known counter-ions, including but not limited to, nitrate, chloride, bromide, fluoride, iodide, sulfate, carbonate, phosphate, and any combination thereof. Examples of suitable salts include calcium chloride, calcium fluoride, calcium bromide, calcium iodide, calcium citrate, calcium gluceptate, calcium gluconate, calcium hydroxide, calcium lactate, calcium phosphate, calcium propionate, calcium acetate, and calcium carbonate. The solution may contain one or more salts. In some embodiments, the salt is a calcium salt. In some embodiments, the anion is chloride. In some embodiments, calcium chloride is the only salt solute. In some embodiments, the salt solute does not contain calcium nitrate or lithium bromide. The amount of the salt in the acid solution may be, for example, about 0.5%, about 1%, about 2%, about 3%, about 4%, about 5%, about 6%, about 7%, about 8%, about 9%, a bout 10%, about 15%, about 20%, about 25% or about 30% (w/v).

Various organic acids or inorganic acids are suitable as solvent of the present method. Non-limiting examples of the acids include formic acid, acetic acid, hydrochloride acid, and any combination thereof. Organic acids as used herein include organic molecules such as phenol that can donate an active proton. Additional examples include propionic acid, butyric acid, valeric acid, caproic acid, oxalic acid, lactic acid, malic acid, citric acid, benzoic acid, carbonic acid, Phenol, uric acid, and any combination of these. The solvent may also contain water as needed to for example promote the dissolution of the salt or the protein. In some embodiments, the acid is formic acid. In some embodiments, the solvent is substantially formic acid by about more than about 90%, more than about 92%, more than about 95%, about 98%, and more than about 99%.

The amount of the salt in the acid solution may vary depending on factors such as the specific type of protein, the amount of the protein and the target composition. Non-limiting embodiments for the range of the salt in the acid solvent include about 1, 2, 3, 4, 5, 6, 7, 8, 9, 10, 12, 14, 16, 18, 20, 25, 30, 35, and 40%. One of ordinary skill in the art can readily adjust the percentage composition of the salt in the solvent without undue experiments.

The dissolution of a protein into the solvent can be promoted by various known methods such as stirring, shaking, sonicating, heating and any combination thereof, which may last from a few seconds to more than 10 hours. In exemplary embodiments, a solution after the addition of a protein is stirred or shaken for about 1, about 2, about 3, about 4, about 5, about 8, about 10, about 15, about 20, about 25, about 30 minutes. Optionally, the solution is then allowed to stand for a time from more than about 1 minute to more than about 30 minutes, all sub-units and sub-ranges included. The insoluble material, bubbles or impurities are next removed from the solution via steps such as decanting the clear portion of the solution, centrifugation, filtration, or any combination thereof. Specific requirements for such steps including for example the size of the filter can be determined by one of ordinary skill in the art without undue experiments.

In some embodiments, an additional non-protein material such as an organic molecule or a polymer may be added to the solution to modify the properties of the final product. Non-limiting examples of non-proteinaceous material include natural & synthetic polymers (e.g. polystyrene, polylactic acid, polyvinylchloride, poly(styrene sulfonate), poly(acrylic acid) (PAA), and/or poly(diallyldimethyl-ammoniumchloride)(PDADMAC), etc), ceramics & glasses (e.g. $SiO_2$, $TiO_2$, CaO, $Al_2O_3$, CuO, ZnO, FeO, MnO, NiO, BaO, SrO, $Fe_2O_3$, etc.), natural & synthetic composites (such as concrete, leather, paper), metals & alloys and combination thereof. Other optional agents that can be incorporated into the protein solution include carbon materials (graphene, nanotubes, nanofibers), fibers, metals, chemicals and/or pharmaceutical agents.

Various types of materials in different shapes can be prepared from the protein solution. In some embodiments, the solution is cast or placed on suitable substrates (e.g. PDMS, Teflon, plastic or metal or alloy). The solvent is allowed to evaporate under ambient condition. To facilitate the removal of the solvent, heating, reduced air pressure, blowing air, or any combination thereof may be applied. In some embodiments, a protein film is formed after molding, spincoating or casting the protein solution in as suitable support substrate. In some embodiments, the protein can be made into a 3-D porous material by freeze-drying. The procedure of freeze-drying is well known in the art and one of ordinary skill can readily adjust the temperature and pressure without undue experiments. Certainly, materials in other shapes can also be prepared from the protein depending on the configuration of the support substrate, the drying condition, and the composition of the protein.

The method of the present invention may also include a compressing step. Compressing under desirable pressure for a sufficient period of time allows manipulation of various protein properties including solvent release temperature, thermal degradation temperature, glass transition temperature, crystallinity, bio-stability, and elastic modulus. By controlling the pressure, the length of compression and the temperature, a desirable range of the above properties can be obtained. It is noted that methods of the present invention may provide proteins with higher glass transition and degradation temperatures even without compression process. After being subject to compression, the processed protein may exhibit additional changes in solvent release temperature, thermal degradation temperature, crystallinity, bio-stability, and mechanical properties.

Various types of commercially available instruments for compression with adjustable pressures can be used in the present invention. Prior to the compressing, the protein may be soaked in water or any aqueous solution, which serves to remove the salt and acid and soften the protein for compressing. The compression pressure may vary depending on the protein composition and the desired use of the protein. Exemplary embodiments of the pressure range include about 1 lb/sq. in. to 1,000,000 lb/sq. in, about 5 lb/sq. in. to 500,000 lb/sq. in, about 10 lb/sq. in. to 500,000 lb/sq. in, about 50 lb/sq. in. to 500,000 lb/sq. in, about 100 lb/sq. in. to 500,000 lb/sq. in, and about 200 lb/sq. in. to 100,000 lb/sq. in, all subunits and sub-ranges included. Non-limiting examples of the pressure include about 1, about 5, about 10, about 20, about 40, about 50, about 60, about 80, about 100, about 200, about 300, about 400, about 500, about 600, about 700, about 800, about 900, about 1000, about 2000, about 3000, about 5000, about 8000, about 10,000, about 15,000, about 20,000, about 25,000, about 30,000, about 50,000, about 80,000, about 100,000, about 200,000, about 300,000, about 400,000, and about 500,000 lb/sq. in.

The duration of compression be last from only a few seconds to over 10 hours. Exemplary ranges of duration include from about 30 seconds to about 24 hours, from less than 1 minute to about 10 hours, from about 1 minute to about 8 hours, from about 1 minute to about 5 hours, from about 1 minute to about 1 hour, from about 10 minutes to about 5 hours, from about 10 minutes to about 2 hours, from about 10 minutes to about 1 hour, from about 20 minutes to about 1 hour, from about 30 minutes to about 1 hour, and from about 45 minutes to about 1 hour, all subranges and subunits included. Other examples include about 1, about 2, about 5, about 10 about 30, about 40 about 50, and about 60 minutes. Further examples include about 1.5, about 2, about 3, about 4, about 5, about 6, about 8, about 10, about 15, and about 20 hours. Heating or cooling may optionally applied to further control the condition of the compression process and the properties of the processed protein. Therefore, by controlling the parameters of the compression process, various properties (e.g. solvent release temperature, thermal degradation temperature, crystallinity, bio-stability (e.g. enzymatic stability), and mechanical properties) of the protein can be modulated or optimized. Exemplary increase in solvent release temperature, glass transition temperature, or thermal degradation temperature resulting from the present invention includes about 0.2, about 0.5° C., about 1° C., about 2° C., about 3° C., about 4° C., about 5° C., about 6° C., about 8° C., about 10° C., about 12° C., about 15° C., about 20° C., about 25° C., about 30° C., about 40° C., and about 50° C. The crystallinity, bio-stability, and mechanical properties of the protein may be improved by, for example, about 1%, about 5%, about 10%, about 15%, about 20%, about 25%, about 30%, about 35%, about 40%, or about 50%. In further examples, the β-sheet of the compressed protein is increase by about 1-70%. About 5-60%, about 10-50%, about 30-50%, about 40-50%, in comparison with uncompressed protein.

In some embodiments, the protein of the present invention, after treatment with the acid solution and/or compression, contains β-sheet in the amount of for example about 5%, about 10%, about 15%, about 20%, about 25%, about 30%, about 35%, about 40%, about 45%, about 50%, about 55%, about 60%, about 65%, about 70, and about 75% or more of the total weight of the protein.

Another aspect of the invention provides a protein, which can be obtained via the process of the present invention. The characteristics of the protein are as described above. For example, the protein may be in the form of a film, a porous material, a block, or any suitable form. In particular, the processed protein exhibits significant changes in properties from unprocessed protein. For example, a higher crystallinity and/or more organized crystal alignment can be observed in processed protein film. The β-sheet (B) contents in protein films can also be increased from about 1 to about 70% after pressing. As described above, the protein of the present invention contains β-sheet in the amount of for example about 5%, about 10%, about 15%, about 20%, about 25%, about 30%, about 35%, about 40%, about 45%, about 50%, about 55%, about 60%, about 65%, about 70, and about 75% or more of the total weight of the protein. Further, the processed protein may become completely insoluble in water, in contrast to being partially soluble prior to being processed. Other properties including solvent evaporation temperature $T_{a1}$, degradation temperature $T_{d2}$, and absorbance may also be changed. In some embodiments, an absorbance peak of the processed protein shows a red shift to lower frequency (e.g. 1640 cm$^{-1}$ shifted to 1620 cm$^{-1}$) on Fourier transform infrared spectrum (FTIR). In some embodiments, only a single absorbance peak shows red shift to lower frequency. As further illustrated in the examples below, the bio-stability of the process protein can also be significantly improved.

Also provided is an article of manufacture containing the above protein obtained through methods of the present invention. Proteins of the present invention demonstrate tunable physical and chemical properties and find applications in for example thermal, mechanical, optical, electrical, chemical, or biomedical compositions and devices. Procedures of incorporating proteins into various products are known in the literature including for example, Hu, et al., Journal of Visualized Experiments, (90), e50891, doi: 10.3791/50891 (2014), the entire disclosure of which is incorporated by reference. A related aspect provides the use of the protein of the present invention in preparing and operating various materials or devices. Examples of the materials or devices include biosensors, nanotubes, nanoparticles, artificial tissues, and drug delivery systems or devices.

The following non-limiting examples set forth herein below illustrate certain aspects of the invention.

Examples

I. Processing of Proteins

Six proteins shown in Table 1 were processed according the procedure below.

a. After the protein fibers being degummed/purified/washed, they were directly put into formic acid+calcium chloride ($CaCl_2$) (4 wt. %) solution, and were shaken several minutes in order to let them dissolved completely. The maximum content that each protein can dissolve in 1 mL formic acid+$CaCl_2$ solution and the following best shaking times to fully dissolve these fibers are described in Table 1a.

b. Then the sample solutions were put on the shelf and stood for a certain period of time (detailed standing times are shown in Table 1a).

c. Further, the protein solutions were centrifuged at 8000 rpm for 10 minutes in order to remove the impurity and bubbles inside the solutions (alternatively, the solution was also poured through a syringe with a 0.45 μm filter after centrifugation in order to control the particle size. However, this procedure is not necessary if the solution has already become transparent without large particles after centrifuging).

d. Finally, the solutions were cast onto substrates (e.g. PDMS, Teflon, Plastic or Aluminum substrates) to dry and form different protein films. (Alternatively, the solution can be further processed to form 3-D porous materials by freeze-drying them at different temperatures).

TABLE 1a

The content, shaking time and standing time of proteins

Figure 7:
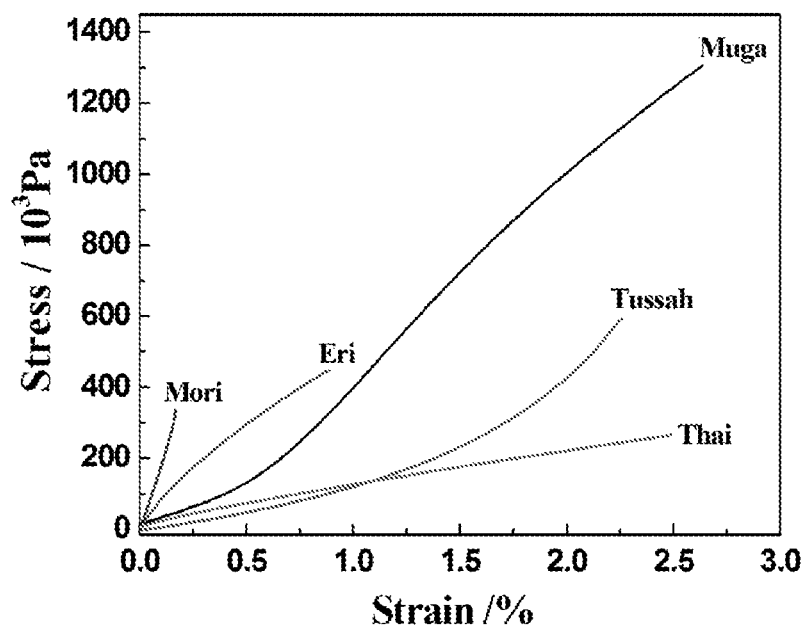
FIG. 7 depicts mechanical tensile tests of different unpressed protein films fabricated with the present method (acid+salt treatment).

| Sample | Content ($g\ ml^{-1}$) | Shaking Time (min.) | Standing Time (min.) |
|---|---|---|---|
| Tussah | 0.10 | >5 | >5 |
| Mori | 0.15 | >1 | >2 |
| Eri | 0.02 | >8 | >8 |
| Muga | 0.08 | >5 | >5 |
| Thai | 0.15 | >1 | >2 |
| Zein | 0.26 | >1 | >2 | e. Furthermore, the cast films exhibited extremely good mechanical flexibility for additional industry processing. The proteins were pressed into thin films under 2-8 tons of weight in a press for several minutes. After pressing, both crystallinity/structures and crystal alignments in the films were changed (see FIG. 7 for the proposed protein molecular and structural model before and after the pressing). The pressing procedure is as follows:

(e1) The film samples were first soaked in water for 5-20 mins. There are two reasons to soak the samples in the water: First, during the soaking, the $CaCl_2$ particles and potential formic acid residues in the films can be fully washed out; Second, the films will absorb some water and become softer, so that the dried soft samples were pressed without breaking them under heavy weight (e.g. 8 tons)

(e2) Then, take the films out of water, and remove the water on the surface of samples by tissue papers or short time (e.g. 5 mins) vacuum drying. (After this procedure, the samples are still very soft but has no surface water)

(e3) Next, the soft films were put under (e.g.) 2-8 tons of weight in a press. The samples were held under the press for 30 mins to make sure the structures and molecular alignments of protein fully and permanently changed. (Note: low weight and short term holding minutes may not fully change the sample properties, sometimes the sample would partially elastically recover if the press weight and holding time is not enough). Besides, the sample thickness and area with different pressing substrates/modes can also be controlled.

(e4) Finally, the pressed protein samples were dried in room temperature or a 37° C. oven for overnight. The samples become harder compared with the just soaked ones.

TABLE 1b

Comparison of two methods: Traditional eater-based solution method vs. Acid + salt (e.g. formic acid + $CaCl_2$) solution method.

Figure 5A:
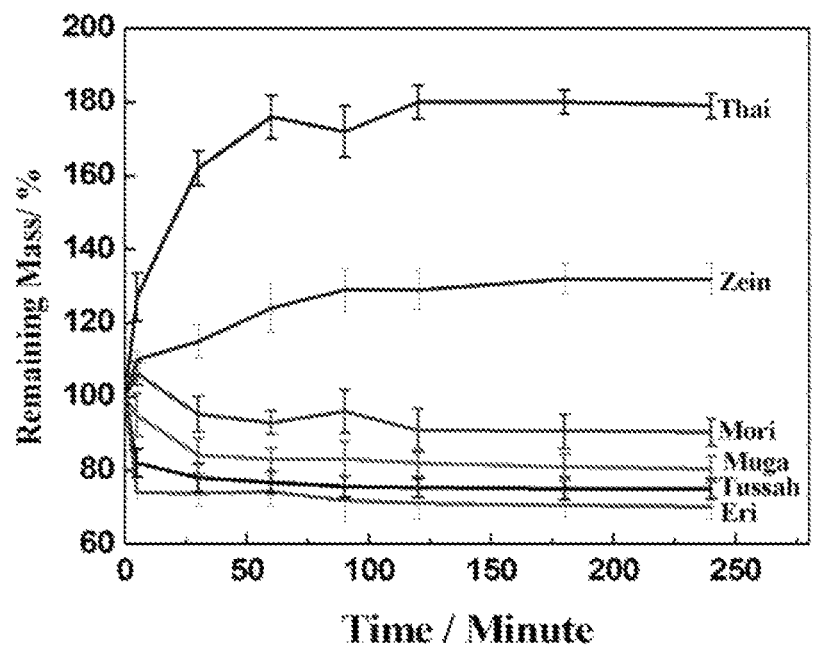
FIG. 5(a)-5(c) depict remaining mass percentage vs. time for (a) unpressed protein films (treated with the present method) swelled in pure water; (b) unpressed protein films (treated with the present method) swelled in protease XIV enzyme solution (N=4, statistical significance, p<0.001) and (c) films fabricated from conventional water-based method and treated by the same protease XIV enzymatic solutions.
Figure 5B:
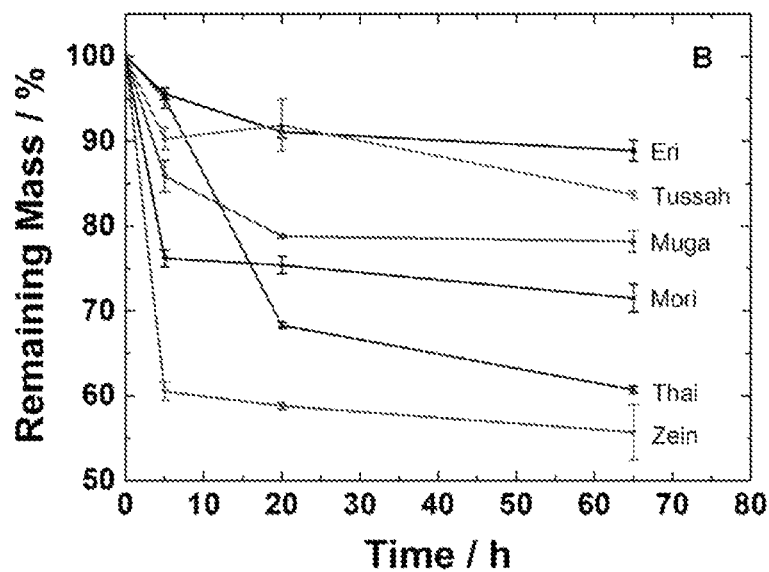

| | New: Formic Acid + $CaCl_2$ based | Old: Water Based |
|---|---|---|
| Time to make final solution | 30 mins | 1 week |
| Time to cast and dry film | 2 h~12 h (<1 day) | 24~48 hs |
| Processing Cost | (Very Low) Only need Formic Acid and $CaCl_2$ for several hours | (High) Need $Ca(NO_3)_2$ (or LiBr), Oven and dialysis system (dialysis tubes, pH solutions, etc.) for at least 3 days |
| Film Flexibility | Most samples can be pressed under 2~8 tons after soaking in water for a few seconds | Very brittle, some samples can not be pressed |
| Water Solubility | Already mostly water insoluble (see FIG. 5) | Still water soluble |
| Enzyme Degradability | Stable in Protease XIV enzyme for a long time (see FIG. 5) | Quickly degraded in specific enzymes |

II. Investigation of Physical Properties of Protein Films

Figure 4A:
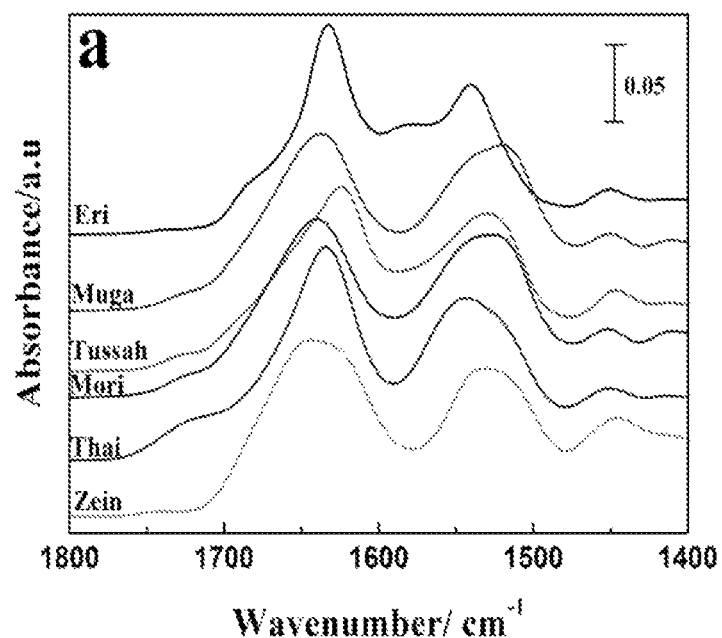
FIGS. 4(a)-4(c) depicts FTIR absorbance spectra of different protein samples (Tussah, Mori, Eri, Muga, Thai silks, and zein) treated with the present method (acid+salt treatment) or water-based method: (a) unpressed protein treated with the present method (b) pressed sample (treated with the present method) spectra in the region of 1400-1800 cm$^{-1}$. (c) a comparison of FTIR absorbance spectra of natural protein fibers, protein films treated with the conventional water-based method (W), and protein films fabricated from this present method (FA) before compression.
Figure 4B:
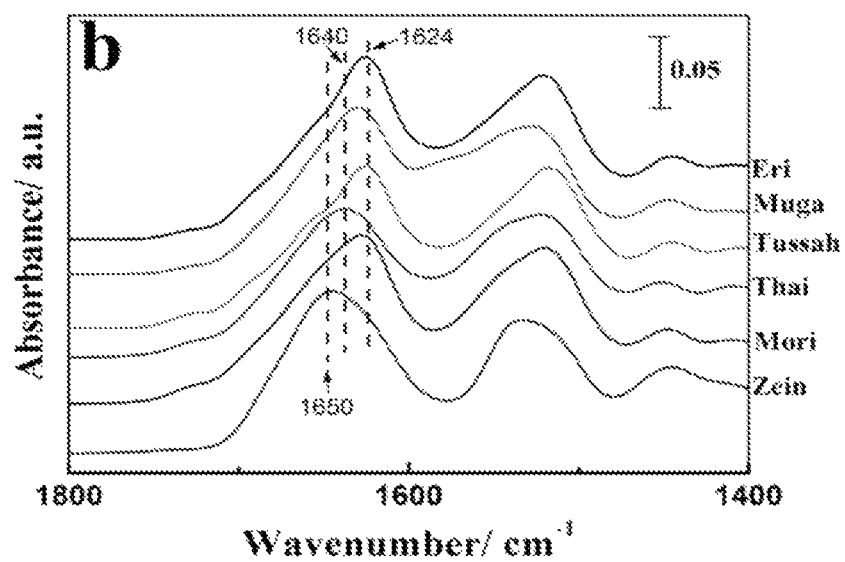
Figure 4C:
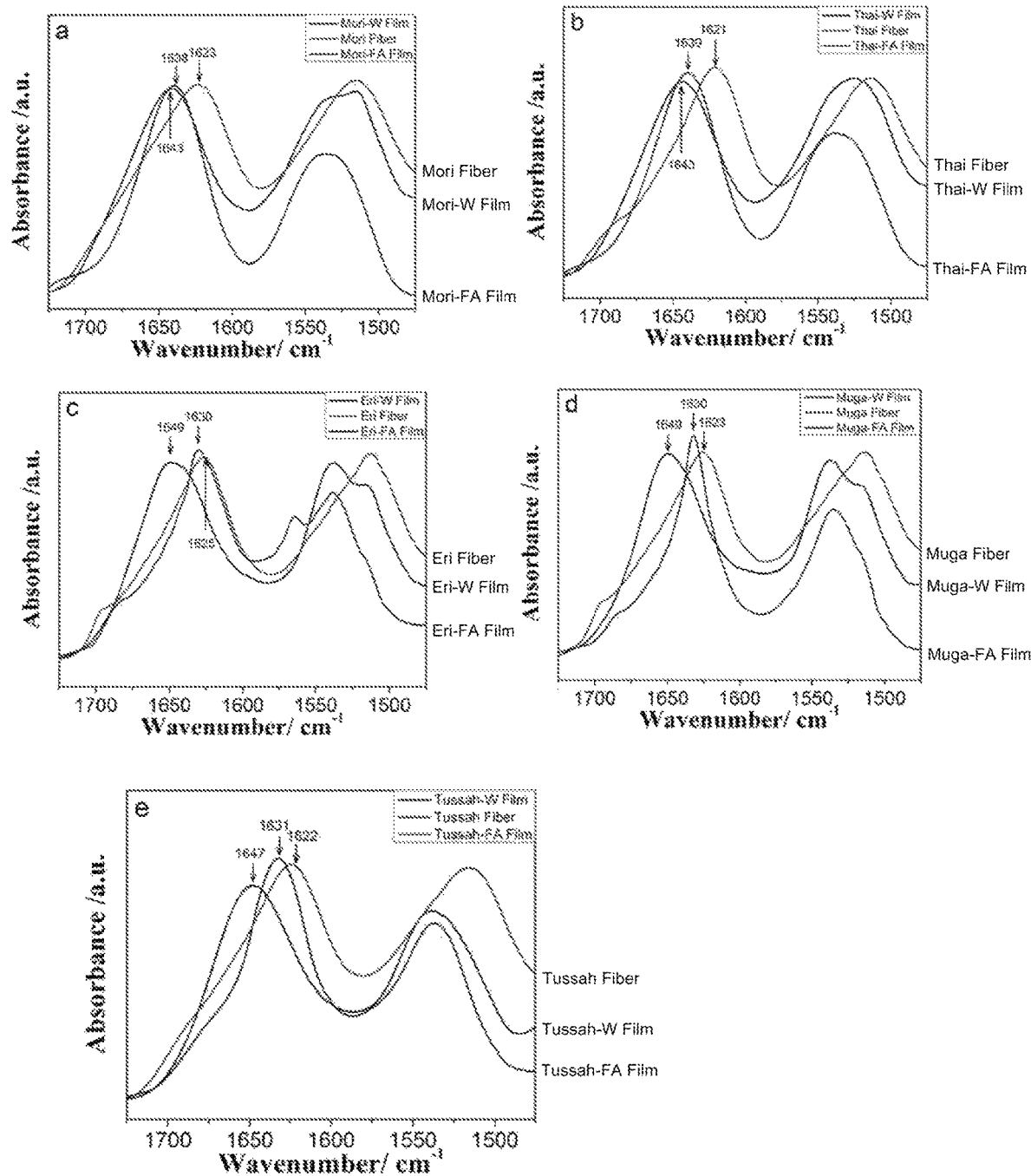
Figure 5C:
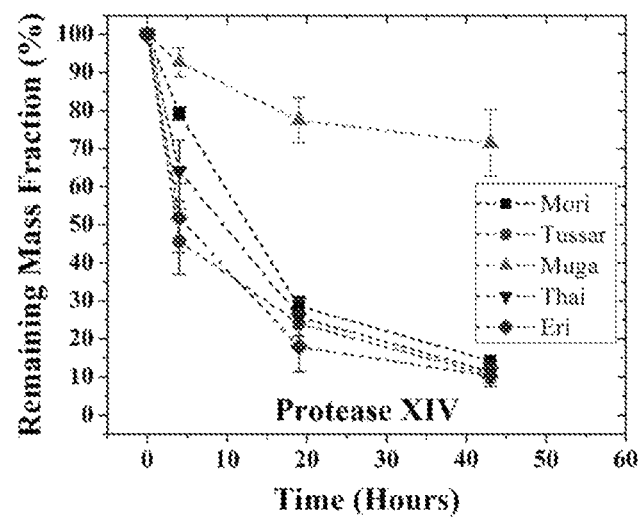
Figures 6A, 6B, 6C, 6D:
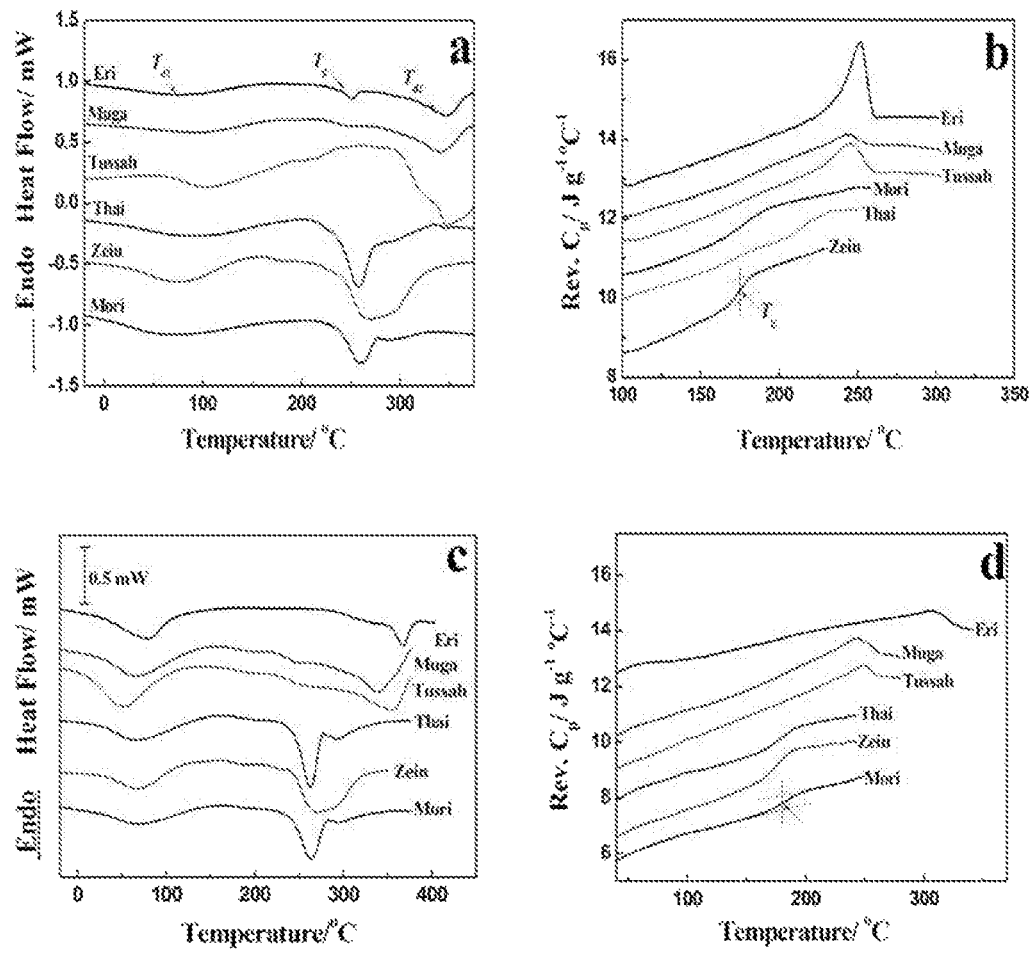
FIG. 6(a)-6(d) depict: (a) Standard DSC scans of different protein samples before the 8-ton pressing. The samples were heated at 2 K min-1 from −30° C. to 400° C., with temperature regions related to solvent evaporations ($T_{d1}$), glass transitions ($T_g$), and sample degradations ($T_{d2}$); (b) Reversing heat capacities of the protein samples before the 8-ton pressing, measured by temperature-modulated DSC (TMDSC) with a 2° C.·min$^{-1}$ heating rate, a modulation period of 60 s and a temperature amplitude of 0.318° C. from −30° C. to 400° C.; (c) Standard DSC scans of the pressed protein films under 8 tons for 30 mins; (d) Reversing heat capacities of the pressed protein films under 8 tons for 30 mins, measured by TMDSC.
Figure 8:
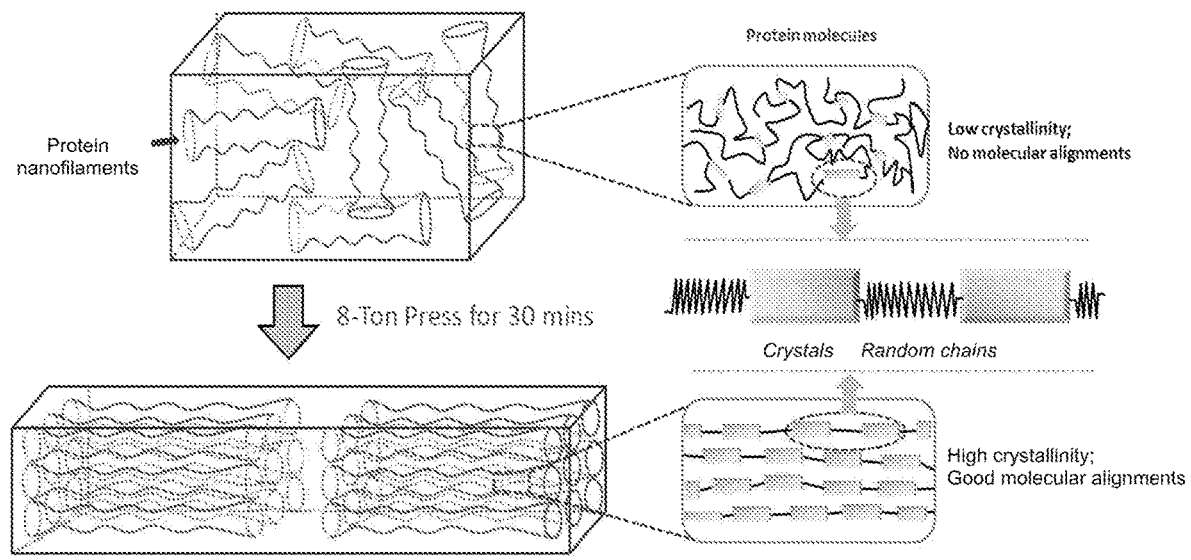
FIG. 8 depicts the effects of pressing on protein films: both crystal structures and molecular alignments of proteins are changed under pressure, resulting in improved physical properties.

Further, the insolubility mechanism of protein films cast from formic acid-$CaCl_2$ solution were studied, and the structural and thermal properties as well as stability of these six protein films were also investigated before and after pressing (including their glass transition temperatures, thermal stability, crystallinities, and water and enzyme degradation profiles etc.). FTIR results (FIG. 4a, b and Table 2) showed that a secondary structural configurations of 6 types of protein films casted from formic Acid-$CaCl_2$ solution. Specifically, after being pressed under 2-8 tons in a press, the content of beta-sheet for all samples increased (see Table 2, column 1, e.g. β-sheet (B) contents in Mori films increased from 9.94% to 49.37% after pressing), which indicated more ordered β-sheet crystals formed in these protein films. FIG. 4c also provided a comparison of FTIR absorbance spectra for natural protein fibers, protein films fabricated from the old water-based method (W), and protein films fabricated from this new acid+salt method (FA) before the pressing. It shows that the new method would help proteins keep part of their β-sheet structures (centered between 1621~1639 $cm^{-1}$) when dissolving their original fibers, which directly bring the films water insolubility after the casting. Fibers treated with the present method and compressed under pressure have a large amount of beta sheet structures (proved by IR absorbance peak centered around 1620 cm−1). Meanwhile, unpressed films using this method have a small amount of beta sheet structures (IR absorbance peak centered around 1630 cm−1) that can help maintain the water insolubility of films. By contrast, the old water-based method completely broke the beta-sheet crystals in protein chains (centered between 1640~1649 $cm^{-1}$), making the cast films soluble in water. The new materials can be mostly insoluble in water before (see FIGS. 5(a) and 5(b)) or after the pressing. For most mass loss in solution, it was largely due to the 4% $CaCl2$, plus the formic acid residues (~5%) in the films. The bulk films have no visible change of morphology after soaking in the water. Some proteins (e.g. Thai, Zein) also absorb water molecules. However, the pressed samples are completely insoluble in water, so a figure is not used to show this. FIG. 5(c) also showed that even water-based films were crystallized by methanol, they will be still more unstable in enzyme solution compared with unpressed protein films fabricated from the new acid-salt method. Furthermore, differential scanning calorimetry results (FIG. 6, Table 3a) showed the glass transition temperatures ($T_g$), solvent release temperatures ($T_{d1}$) and the degradation temperatures ($T_{d2}$) of six protein film samples before (FIG. 6a,b) and after (FIG. 6c,d) the pressing. It is found that their glass transition temperature $T_g$ did not significantly change before and after pressing. However, both solvent evaporation temperature $T_{d1}$ and degradation temperature $T_{d2}$ of proteins changed obviously after the 2-8 tons pressing treatment in a carver. Table 3b also compared thermal data of different protein films produced by the old water-based method and the new acid+salt method before the pressing. The new method always produces more stable films with higher glass transition and degradation temperatures. Finally, mechanical properties of unpressed protein films fabricated from this new method were demonstrated in FIG. 7 and Table 4. To better explain the effect of pressing to the protein samples produced by this new acid+salt method, a molecular model (FIG. 8) was provided to interpret how the pressing procedure improves the structures of molecular alignments of samples.

TABLE 2

Percentages of secondary structures before and after pressing in different new protein films calculated by a FTIR deconvolution method developed previously (Hu et al. Macromolecules, 2006, 39, pp 6161-6170).

| Sample | β-sheet (B) | α-helix & random coils (A + R) | Turns (T) | Side chains (S) |
|---|---|---|---|---|
| Tussah | 47.41/49.76[P] | 48.11 | 3.80 | 0.68 |
| Mori | 9.94/49.37[P] | 62.55 | 26.86 | 0.65 |
| Eri | 46.89/51.80[P] | 41.49 | 4.48 | 7.14 |
| Muga | 37.82/47.89[P] | 47.64 | 11.54 | 3.01 |
| Thai | 9.73/40.20[P] | 69.75 | 24.62 | 0.90 |
| Zein | 13.45/35.10[P] | 45.40 | 15.78 | 3.72 |

[P]Beta-sheet percentages after being pressed under 2~8 tons in a press.
*All calculated secondary structure fractions have a same unit (wt %) with a ±2 wt % error bar;

TABLE 3a

Thermal analysis data of different protein films (using new acid + salt method) before and after pressing:

| Protein Sample | $T_g$/° C. | Solvent release $T_{d1}$/° C. | Degradation $T_{d2}$/° C. |
|---|---|---|---|
| Eri | 226.3[F,P] | 110.3[F,P] | 346.1[F,P] |
| Mori | 189.2[F,P] | 171.9[F]/77.48[P] | 260.2[F]/252.2[P] |
| Muga | 218.1[F,P] | 125.5[F]/72.48[P] | 341.6[F]/334.9[P] |
| Tussah | 224.5[F,P] | 103.9[F]/76.6[P] | 345.4[F]/338.2[P] |
| Thai | 216.6[F,P] | 126.6[F]/75.78[P] | 266.8[F]/264.7[P] |
| Zein | 173.6[F,P] | 120.2[F]/70.75[P] | 259.3[F]/277.2[P] |

[F]Glass transition temperature $T_g$, solvent evaporation temperature $T_{d1}$ and degradation temperature $T_{d2}$ of unpressed protein samlpess fabricated by this present method;
[P]Glass transition temperature $T_g$, solvent evaporation temperature $T_{d1}$ and degradation temperature $T_{d2}$ of these new protein samples after the 2~8 tons pressing treatment in a press.

TABLE 3b

Thermal property comparisons of different protein films produced by the old and the new methods: the superscript 'F' stands for samples manufactured by the new acid + salt method before the pressing, and 'W' stands for samples manufactured by the old water-based method.*

| Protein Sample | $T_g$/° C. | $\Delta C_p$ at $T_g$/J $g^{-1}$ $K^{-1}$ | Degradation $T_{d2}$/° C. | Onset temperature of decomposition/° C. | Degradation Middle Temperature $T_{dm}$/° C. | Remaining mass at 400° C./% |
|---|---|---|---|---|---|---|
| Eri | 238.8[F]/176.0[W] | 0.041[F]/0.509[W] | 346.1[F]/329.0[W] | 327.0[F] | 372.7[F] | 47.42[F] |
| Muga | 232.4[F]/168.0[W] | 0.135[F]/0.370[W] | 341.6[F]/330.3[W] | 384.8[F] | 396.6[F] | 49.24[F] |
| Tussah | 233.9[F]/188.0[W] | 0.019[F]/0.282[W] | 345.4[F]/336.6[W] | 319.1[F] | 375.3[F] | 49.26[F] |
| Thai | 217.8[F]/149.0[W] | 0.388[F]/0.564[W] | 266.8[F]/245.4[W] | 306.0[F] | 328.3[F] | 54.06[F] |
| Mori | 176.3[F]/175.0[W] | 0.483[F]/0.475[W] | 260.2[F]/244.3[W] | 300.3[F] | 313.8[F] | 26.32[F] |

TABLE 3b-continued

Thermal property comparisons of different protein films produced by the old and the new methods: the superscript 'F' stands for samples manufactured by the new acid + salt method before the pressing, and 'W' stands for samples manufactured by the old water-based method.*

| Protein Sample | $T_g/°C$ | $\Delta C_p$ at $T_g/J\ g^{-1}\ K^{-1}$ | Degradation $T_{d2}/°C$ | Onset temperature of decomposition/°C | Degradation Middle Temperature $T_{dm}/°C$ | Remaining mass at 400°C./% |
|---|---|---|---|---|---|---|

*All numbers have an error bar within ±5%. The first four columns ($T_g$, $\Delta C_p$ at $T_g$, and degradation $T_{d2}$) were determined by DSC analysis, the rest were determined by thermogravimetric (TG) analysis. $T_g$ and $T_{d2}$ represented the glass transition temperature, solvent release peak temperature and thermal degradation peak temperatures of different protein films. (Note: the glass transition temperatures ($T_g$) of new films based on organic acid + salt (F) are generally higher than those of conventional water-based protein films (W) described in Table 1b)

TABLE 4

Mechanical properties of different protein films fabricated from the new acid + salt method

| Sample | Elastic Modulus (×MPa) |
|---|---|
| Tussah | 11.44 |
| Muga | 25.25 |
| Eri | 80.56 |
| Mori | 172.92 |
| Thai | 13.48 |

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

The invention claimed is:

1. A method of processing a protein, the method comprising:
   a) dissolving a protein in a solution comprising an acid and a salt of at least one of an alkaline earth metal and an alkali metal, to yield a protein solution;
   b) removing the acid from the protein solution to yield a processed protein;
   c) compressing the processed protein by applying pressure in the range of about 10 lb/sq. in to about 500,000 lb/sq. in. to yield a compressed protein;
      wherein the protein solution further comprises a non-proteinaceous material selected from the group consisting of polymers, ceramics, glasses, composites, metals, alloys, and any combinations thereof.

2. The method of claim 1, wherein removing the acid from the protein solution comprises evaporating the acid from the protein solution.

3. The method of claim 1, wherein the acid is selected from the group consisting of formic acid, acetic acid, hydrochloric acid, propionic acid, butyric acid, valeric acid, caproic acid, oxalic acid, lactic acid, malic acid, citric acid, benzoic acid, carbonic acid, phenol, uric acid, and any combinations thereof.

4. The method of claim 1, wherein the salt is selected from the group consisting of calcium chloride, calcium fluoride, calcium bromide, calcium iodide, calcium citrate, calcium gluceptate, calcium gluconate, calcium hydroxide, calcium lactate, calcium phosphate, calcium propionate, calcium acetate, and calcium carbonate.

5. The method of claim 1, wherein the protein is from a source selected from the group consisting of silks, corn zeins, collagens, elastins, keratins, resilins, reflectins, plant and soy proteins, and any combinations thereof.

6. The method of claim 1, wherein the protein is a natural protein.

7. The method of claim 1, wherein the protein is a recombinant protein.

8. The method of claim 1, further comprising adding to the protein solution one or more agents selected from the group consisting of graphene, nanotubes, nanofibers, nanoparticles, metal particles, a chemical agent, and a pharmaceutical agent.

9. The method of claim 1, wherein the protein solution contains about 0.5-10% salt (w/v).

10. The method of claim 1, wherein the protein solution contains about 0.5% to about 50% (w/v) of the protein.

11. The method of claim 1, wherein the processed protein is soaked in water prior to being compressed.

12. The method of claim 1, wherein the pressure is selected to optimize at least one protein characteristic selected from the group consisting of solvent release temperature, thermal degradation temperature, crystallinity, biostability, elastic modulus, and any combinations thereof.

13. A processed protein produced by the method of claim 1.

14. The processed protein of claim 13, wherein the processed protein exhibits a higher crystallinity relative to its unprocessed form.

15. The processed protein of claim 13, wherein the processed protein is insoluble in water.

16. The processed protein of claim 13, wherein the processed protein has about 1% to about 70% higher β-sheet content than the unprocessed protein.

17. The processed protein of claim 13, wherein the processed protein exhibits a red-shift in absorbance wavelength (to a lower frequency) relative to the unprocessed protein.

18. The method of claim 1, wherein any insoluble material or impurities are separated from the protein solution before the acid is removed from the protein solution.

19. The method of claim 1, wherein the protein solution is allowed to stand for about 2 mins. to about 8 mins. before the acid is removed from the protein solution.

20. The method of claim 1, wherein the pressure is applied to the processed protein for about 30 seconds to about 24 hours.

21. The method of claim 1, wherein the processed protein has higher crystallinity than the unprocessed protein.

22. The method of claim 1, wherein the processed protein has about 1% to about 70% higher β-sheet content than the unprocessed protein.

23. The method of claim 1, wherein the compressed protein is further dried.

24. A method of processing a protein, the method comprising:
   a) dissolving a protein in a solution comprising an acid and a salt of at least one of an alkaline earth metal and an alkali metal, to yield a protein solution;
   b) removing the acid from the protein solution to yield a processed protein;
   c) compressing the processed protein by applying pressure in the range of about 10 lb/sq. in to about 500,000 lb/sq. in. to yield a compressed protein;
   wherein the protein is a recombinant protein.

25. The method of claim 24, wherein removing the acid from the protein solution comprises evaporating the acid from the protein solution.

26. The method of claim 24, wherein the acid is selected from the group consisting of formic acid, acetic acid, hydrochloride acid, propionic acid, butyric acid, valeric acid, caproic acid, oxalic acid, lactic acid, malic acid, citric acid, benzoic acid, carbonic acid, phenol, uric acid, and any combinations thereof.

27. The method of claim 24, wherein the salt is selected from the group consisting of calcium chloride, calcium fluoride, calcium bromide, calcium iodide, calcium citrate, calcium gluceptate, calcium gluconate, calcium hydroxide, calcium lactate, calcium phosphate, calcium propionate, calcium acetate, and calcium carbonate.

28. The method of claim 24, wherein the protein is from a source selected from the group consisting of silks, corn zeins, collagens, elastins, keratins, resilins, reflectins, plant and soy proteins, and any combinations thereof.

29. The method of claim 24, wherein the protein solution further comprises a non-proteinaceous material.

30. The method of claim 29, wherein the non-proteinaceous material is selected from the group consisting of polymers, ceramics, glasses, composites, metals, alloys, and any combinations thereof.

31. The method of claim 24, further comprising adding to the protein solution one or more agents selected from the group consisting of graphene, nanotubes, nanofibers, nanoparticles, metal particles, a chemical agent, and a pharmaceutical agent.

32. The method of claim 24, wherein the protein solution contains about 0.5% to about 50% (w/v) of the protein.

33. The method of claim 24, wherein the processed protein is soaked in water prior to being compressed.

34. The method of claim 24, wherein the pressure is selected to optimize at least one protein characteristic selected from the group consisting of solvent release temperature, thermal degradation temperature, crystallinity, biostability, elastic modulus, and any combinations thereof.

35. The method of claim 24, wherein any insoluble material or impurities are separated from the protein solution before the acid is removed from the protein solution.

36. The method of claim 24, wherein the protein solution is allowed to stand for about 2 mins. to about 8 mins. before the acid is removed from the protein solution.

37. The method of claim 24, wherein the pressure is applied to the processed protein for about 30 seconds to about 24 hours.

38. The method of claim 24, wherein the processed protein has higher crystallinity than the unprocessed protein.

39. The method of claim 24, wherein the processed protein has about 1% to about 70% higher β-sheet content than the unprocessed protein.

40. The method of claim 24, wherein the compressed protein is further dried.

* * * * *